(12) United States Patent
Wochele

(10) Patent No.: US 9,833,356 B2
(45) Date of Patent: Dec. 5, 2017

(54) DISPENSER FOR DISPENSING PHARMACEUTICAL LIQUIDS

(71) Applicant: Matthias Wochele, Friolzheim (DE)

(72) Inventor: Matthias Wochele, Friolzheim (DE)

(73) Assignee: APTAR RADOLFZELL GMBH, Radolfzell (DE)

(*) Notice: Subject to any disclaimer, the term of this patent is extended or adjusted under 35 U.S.C. 154(b) by 370 days.

(21) Appl. No.: 14/359,501

(22) PCT Filed: Nov. 8, 2012

(86) PCT No.: PCT/EP2012/072138
§ 371 (c)(1),
(2) Date: May 20, 2014

(87) PCT Pub. No.: WO2013/075951
PCT Pub. Date: May 30, 2013

(65) Prior Publication Data
US 2014/0336596 A1 Nov. 13, 2014

(30) Foreign Application Priority Data
Nov. 21, 2011 (DE) .................. 10 2011 086 755

(51) Int. Cl.
*A61F 9/00* (2006.01)
*B65D 47/20* (2006.01)
(Continued)

(52) U.S. Cl.
CPC ............. *A61F 9/0008* (2013.01); *A61J 1/067* (2013.01); *B65D 47/20* (2013.01);
(Continued)

(58) Field of Classification Search
CPC .................................................. A61J 1/1443
See application file for complete search history.

(56) References Cited

U.S. PATENT DOCUMENTS

| 1,666,402 A | * | 4/1928 | Wood | .............. B65D 35/20 137/539 |
| 2,015,794 A | * | 10/1935 | Gray | .............. B65D 35/20 222/496 |

(Continued)

FOREIGN PATENT DOCUMENTS

| CA | 2 492 255 A1 | 7/2006 |
| CN | 1326399 A | 12/2001 |

(Continued)

OTHER PUBLICATIONS

Office Action of Chinese Patent Office issued in Application No. 201280057236.8, dated Apr. 27, 2015 (5 pages).

(Continued)

*Primary Examiner* — Paula L Craig
(74) *Attorney, Agent, or Firm* — Flynn, Thiel, Boutell & Tanis, P.C.

(57) ABSTRACT

Dispenser for dispensing pharmaceutical liquid having a housing, a liquid reservoir arranged within the housing, an exit opening through which liquid is discharged into a surrounding atmosphere, an outlet channel connecting the liquid reservoir to the exit opening and having an outlet valve, openable in a pressure-dependent manner or actuatable manually, arranged in the outlet channel. With the valve closed, the outlet channel is subdivided into a first portion upstream of the outlet valve and a second portion downstream of the outlet valve. The housing is of antibacterial design in the region of surfaces which are intended to come into contact with the liquid, wherein it is exclusively surfaces in the region of the second portion and/or of an outer surface of the housing which have this antibacterial design.

17 Claims, 3 Drawing Sheets

(51) Int. Cl.
*A61J 1/06* (2006.01)
*A61J 1/14* (2006.01)
*A61J 1/20* (2006.01)

(52) U.S. Cl.
CPC ........... *B65D 47/2068* (2013.01); *A61J 1/145* (2015.05); *A61J 1/1425* (2015.05); *A61J 1/1443* (2013.01); *A61J 1/2037* (2015.05); *A61J 1/2075* (2015.05)

(56) References Cited

U.S. PATENT DOCUMENTS

| | | | | |
|---|---|---|---|---|
| 2,715,980 | A | * | 8/1955 | Frick ................ B65D 49/08 137/853 |
| 2,974,835 | A | * | 3/1961 | Herbrick ............ B65D 47/242 222/507 |
| 4,485,064 | A | * | 11/1984 | Laurin ............... A61J 1/1443 215/317 |
| 4,739,906 | A | * | 4/1988 | Loturco ............. A61J 1/1443 222/212 |
| 5,013,459 | A | | 5/1991 | Gettings et al. |
| 5,154,325 | A | * | 10/1992 | Ryder ............... B05B 11/0021 222/189.06 |
| 5,197,638 | A | * | 3/1993 | Wood ................ B65D 35/20 137/510 |
| 5,232,687 | A | | 8/1993 | Geimer |
| 5,360,145 | A | | 11/1994 | Gueret |
| 5,611,464 | A | * | 3/1997 | Tsao ................ A61K 9/0048 222/189.06 |
| 5,648,084 | A | * | 7/1997 | Guttag .............. A61K 9/0048 424/400 |
| 5,829,645 | A | * | 11/1998 | Hennemann ........ B05B 11/0021 210/198.1 |
| 5,950,877 | A | * | 9/1999 | Garcia ............... A61M 15/08 222/190 |
| 5,992,701 | A | | 11/1999 | Bougamont et al. |
| 6,053,368 | A | * | 4/2000 | Geimer .............. A61L 2/16 141/285 |
| 6,129,248 | A | | 10/2000 | Hagele |
| 6,227,413 | B1 | | 5/2001 | Bommer |
| 6,666,355 | B2 | * | 12/2003 | Padar ................ B05B 11/0016 141/65 |
| 6,695,173 | B1 | * | 2/2004 | Fontana ............. B65D 47/2068 222/206 |
| 7,213,727 | B2 | | 5/2007 | Kokubo |
| 7,249,693 | B2 | | 7/2007 | Buxmann |
| 7,306,129 | B2 | | 12/2007 | Swiss et al. |
| 7,513,396 | B2 | | 4/2009 | Pardes et al. |
| 7,578,388 | B2 | | 8/2009 | O'Connell et al. |
| 7,874,467 | B2 | | 1/2011 | Pardes et al. |
| 7,997,460 | B2 | | 8/2011 | Pardes et al. |
| 8,087,553 | B2 | | 1/2012 | Pardes et al. |
| 8,444,027 | B2 | | 5/2013 | Pardes et al. |
| 8,894,622 | B2 | | 11/2014 | Chibret et al. |
| 9,402,765 | B2 | | 8/2016 | Chibret et al. |
| 2004/0079766 | A1 | | 4/2004 | Kokubo |
| 2004/0200860 | A1 | | 10/2004 | Buxmann |
| 2005/0154361 | A1 | * | 7/2005 | Sabesan ............ A01N 43/16 604/365 |
| 2005/0173459 | A1 | | 8/2005 | Buxmann |
| 2006/0043116 | A1 | | 3/2006 | Kawashiro et al. |
| 2007/0095862 | A1 | | 5/2007 | Swiss et al. |
| 2007/0113841 | A1 | * | 5/2007 | Fuchs ................ A61F 9/0008 128/200.14 |
| 2008/0135586 | A1 | | 6/2008 | Pardes et al. |
| 2008/0264827 | A1 | | 10/2008 | O'Connell et al. |
| 2009/0152306 | A1 | | 6/2009 | Pardes et al. |
| 2009/0218373 | A1 | * | 9/2009 | Pardes ............... B65D 47/18 222/494 |
| 2009/0236374 | A1 | | 9/2009 | Pardes et al. |
| 2009/0250492 | A1 | | 10/2009 | Pardes et al. |
| 2009/0294347 | A1 | * | 12/2009 | Wochele ............ B05B 11/0021 210/244 |
| 2009/0321479 | A1 | * | 12/2009 | Fontana ............. B65D 47/20 222/494 |
| 2011/0056993 | A1 | | 3/2011 | Lee et al. |
| 2011/0068133 | A1 | | 3/2011 | Painchaud et al. |
| 2011/0125111 | A1 | | 5/2011 | Chibret et al. |
| 2011/0155770 | A1 | | 6/2011 | Painchaud et al. |
| 2012/0111899 | A1 | | 5/2012 | Pardes et al. |
| 2012/0312840 | A1 | * | 12/2012 | Hasegawa ........... A61M 31/00 222/215 |
| 2013/0140225 | A1 | | 6/2013 | Decock et al. |
| 2015/0150719 | A1 | | 6/2015 | Chibret et al. |

FOREIGN PATENT DOCUMENTS

| | | |
|---|---|---|
| CN | 101351387 A | 1/2009 |
| DE | 20 2004 013 331 U1 | 3/2005 |
| EP | 0 864 371 A1 | 9/1998 |
| EP | 1 466 668 A1 | 10/2004 |
| EP | 1 541 487 A1 | 6/2005 |
| FR | 2 934 572 A1 | 2/2010 |
| JP | 62-182247 U | 11/1987 |
| JP | 10-278936 A | 10/1998 |
| JP | 2004-196417 A | 7/2004 |
| JP | 2006-175199 A | 7/2006 |
| JP | 2007-7324 A | 1/2007 |
| WO | WO 00/29192 A2 | 5/2000 |
| WO | WO 01/83010 A1 | 11/2001 |
| WO | WO 2004/011345 A1 | 2/2004 |
| WO | WO 2009/109370 A1 | 9/2009 |
| WO | WO 2009/130411 A1 | 10/2009 |
| WO | WO 2010/013131 A1 | 2/2010 |
| WO | WO 2012/013894 A1 | 2/2012 |

OTHER PUBLICATIONS

Form PCT/ISA/210 issued in PCT/EP2012/072138 dated Jan. 31, 2013 with English Translation (8 pages).
Examination Report from the German Patent Office issued in Appln. No. DE 10 2011 086 755.4 dated Jan. 3, 2012 (5 pages).
Japanese Office Action issued in Appln. No. 2014-542763 dated May 17, 2016 with English translation (9 pages).
European Patent Office Letter issued in Application No. 12790468.8 dated May 2, 2017 (1 page).
European Patent Office Opposition Letter issued in Application No. 12790468.8 dated Apr. 20, 2017 and forwarded by the European Patent Office on May 2, 2017 (39 pages).

* cited by examiner

DISPENSER FOR DISPENSING PHARMACEUTICAL LIQUIDS

FIELD AND BACKGROUND OF THE INVENTION

The invention relates to a dispenser for dispensing pharmaceutical liquids. Such a dispenser comprises a housing, a liquid reservoir arranged within the housing, an exit opening through which the liquid can be discharged into a surrounding atmosphere, an outlet channel connecting the liquid reservoir to the exit opening, and an outlet valve. The outlet valve can be opened in a pressure-dependent manner or can be actuated manually, and is arranged in the outlet channel and, with the outlet valve closed, subdivides the outlet channel into a first portion upstream of the outlet valve and a second portion downstream of the outlet valve.

Dispensers of the type in question are known in general from the prior art. They have a liquid reservoir, from which liquid can be delivered in the direction of the exit opening, it being possible for this to take place via a large number of different mechanisms. It is thus possible for the liquid reservoir to be designed in the form of a squeezy bottle, of which the contents can be subjected to pressure as a result of the walls being deformed. It is also possible to use a separate pumping device. Dispensers of the type in question have an outlet valve. This is a valve which is arranged in the path of the liquid immediately upstream of the outlet opening. It is usually an outlet valve which can be opened in a pressure-dependent manner, the valve being opened as a result of the liquid in the liquid reservoir, or a sub-quantity removed therefrom, being subjected to pressure and closing automatically again as soon as the corresponding positive pressure in relation to the surroundings is done away with. However, it is also possible here, in principle, to use other types of valves. It is thus possible, for example, to provide for the liquid in the liquid reservoir to be subjected to permanent pressure and for the dispenser to be handled using a handle which can be actuated manually to open the outlet valve.

In the dispenser of the type in question, the outlet valve, once closed, does not allow any liquid which has passed into the second portion of the outlet channel, or which has remained in the environment of the exit opening outside the outlet channel, to be taken back into the dispenser. This prevents any possible contamination of the contents of the liquid reservoir as a result of liquid residues being taken back in.

The residual liquid therefore remains in a region which is accessible from the outside. However, there is a risk of contamination here.

In order to avoid contamination in particular in the case of preservative-free liquids, it is already known, in principle, from the prior art for the dispenser to be provided with antibacterial surfaces which come into contact with the liquid. A description is given of this, for example, in U.S. Pat. No. 5,232,687, of which the exemplary embodiment describes a dispenser which has an outlet valve of antibacterial design.

It has been found in the past, however, that configuring surfaces with antibacterial qualities may also have problematic secondary effects. Depending on the ways and means of configuring the antibacterial surfaces, it should be noted that constituent parts of the correspondingly designed surface detach from the latter and pass into the liquid. They are then dispensed together with the liquid. This is disadvantageous from a medical point of view.

OBJECT AND SOLUTION

It is therefore an object of the invention to provide a dispenser of the type in question in which the problems related to contamination of the liquid are alleviated.

This is achieved according to the invention in that the housing is of antibacterial design in the region of surfaces which are intended to come into contact with the liquid, wherein it is exclusively surfaces in the region of the second portion of the outlet channel and/or in the region of an outer surface of the housing which have this antibacterial design.

In the case of a dispenser according to the invention, provision is thus made that it is specifically only such surfaces as are not in permanent contact with all the liquid contained in the dispenser which are of antibacterial design. Instead, the antibacterial effect which stems from the correspondingly designed surfaces should relate exclusively to that liquid which is already arranged on the far side of the outlet valve and therefore, on the one hand, cannot pass back into the liquid reservoir and, on the other hand, may be exposed to contamination to a certain extent on account of being arranged on the far side of the outlet valve.

In the case of a dispenser according to the invention, the liquid, which is located in the liquid reservoir and the liquid regions between the liquid reservoir and the outlet valve, is protected against contamination in that the outlet valve and a possible air inlet are designed such that contamination cannot pass into the dispenser. It is therefore possible, so as to avoid the aforementioned secondary effects, to dispense with a specific bactericidal configuration within the dispenser. It is merely the liquid residues on the far side of the outlet valve that are protected against contamination by surface configurations which kill bacteria, or prevent the growth thereof, being provided there. It has been found that combining these measures can ensure particularly good liquid quality.

As an example, the following option is provided in order to achieve the antibacterial configuration of the relevant surfaces: it is thus possible to provide the surface with silver in its metallic form or in the form of a silver compound, with silver salts, silver chlorides, silver sulfadiazine, silver oxides or a silver alloy. It is also possible to use nanometal particles, in particular nanosilver particles. It is also expedient to use a biguanide derivative, chlorohexidine diacetate or chlorohexidine digluconate. It is also possible to use quaternary ammonium compounds such as benzalkonium chloride and stearalkonium chloride in order to achieve the anti-pathogen action. Also in existence are expediently usable organic dyes with antiseptic action, which can be used here. These include, for example, toluidine blue, methylene blue, gentian violet and acridine and related active substances such as acridine orange and acridine yellow as well as ethacridine lactate. Germicidal polymers such as polyhexanide are also possible. A further option consists in providing material of the appropriate component, or the applied coating, with additives which contain metal-organic substances with an ionizing effect. Such additives are marketed, for example, under the name "SteriOne" by a company of the same name.

As a result of the surfaces provided on the far side of the outlet valve being configured correspondingly, the liquid residue, in particular the residual droplet, which remains here once a droplet has been discharged by means of a droplet dispenser is effectively shielded from contamination.

A particularly important configuration is the configuration according to the invention in conjunction with a dispenser which is designed in the form of a droplet dispenser and has a droplet-forming surface which encloses the exit opening and is bounded on the outside by a separation edge. In the case of such a droplet dispenser, the aforementioned residual droplet remains more or less unavoidably on the droplet-forming surface as a result of physical conditions. This is a risk in particular in conjunction with droplet dispensers for introducing liquid into the eye, since contamination of the liquid has a particularly critical effect here.

The configuration according to the invention is therefore particularly advantageous in the case of such droplet dispensers. This applies in particular to droplet dispensers of which the liquid reservoir is filled with a liquid which serves for treating eye diseases. The liquid here may be, for example, a liquid with one of the following active substances: ranibizumab, latanoprost, travoprost, ciclosporine, bimatoprost, olopatadine, dorzolamide, moxifloxacin, brimonidine, hyaluronic acid, brinzolamide, dexamethasone, levofloxacin, gatifloxacin, cellulose and verteporfin.

A variant which is considered to be particularly advantageous for the purpose of configuring a surface arranged on the far side of the outlet valve is one in which the second portion of the outlet channel is formed, at least in part, by an antibacterial insert which is designed in the form of a component which is separate from the first portion and the functional parts of the valve. Such an insert may be provided, for example, in the form of a tubular or annular component of which the inner wall forms part of the second portion of the outlet channel. The use of such a comparatively small component, which is provided in respect of the antibacterial configuration of the dispenser, permits, with comparatively low outlay, to use otherwise structurally identical dispensers with or without an antibacterial insert or to use an insert which has been adapted to particularly good effect to the liquid used. It is thus possible to use more or less structurally identical dispensers for different application purposes and for said dispensers to differ from one another primarily merely in respect of the insert.

The aforementioned insert is preferably pushed through the exit opening, counter to the exit direction of the liquid, into a recess of the housing, said recess being adapted to the external shape of the insert. It can be retained here by means of a form fit, which can be produced for example by a latching connection, or else purely by a frictional fit.

It is possible here for the insert, by way of an outwardly oriented end side, to form, at the same time, part of the droplet-forming surface or the entire droplet-forming surface, and therefore it is not just the liquid residues remaining in the outlet channel, but also the residual droplet in the region of the droplet-forming surface, which are/is in direct contact with the antibacterial surface of the insert.

Instead of such a solution in which the insert, in the form of a carrier of the antibacterial surfaces, is pushed into a recess, it may also be advantageous, in the case of an alternative configuration, if the housing has an antibacterial attachment which is pushed, in the region of the dispensing opening, onto a housing part through which the second portion of the outlet valve penetrates. This second configuration thus provides a functionally suitable dispenser which is suitable for dispensing liquid even without the aforementioned attachment. Functionality in respect of the antibacterial properties, however, can be supplemented by the aforementioned attachment in the pushed-on state. A latching connection may be provided in order to secure the attachment to the corresponding housing part. It is advantageous, however, if the outside of said housing part acting as a carrier is of at least partially cylindrical or slightly conical (angle <3°) design, and therefore the attachment is retained in the envisaged position purely with a frictional fit.

In the case of a droplet dispenser, the attachment forms preferably the entire droplet-forming surface, as a result of which, alongside the advantage of the antibacterial configuration, exchanging the insert also permits shaping of the droplet-forming surface on a case by case basis and leaves the dispenser otherwise unchanged.

In the case of a further variant of the invention, provision is made for the second portion of the outlet channel to contain a porous insert, which has the liquid flowing through it when said liquid is delivered from the outlet valve to the outlet opening. Such a porous insert has a very large surface area, with which the residual droplet, or the liquid remaining in the outlet channel, comes into contact, and therefore the antibacterial effect of such a porous insert is very good. The insert, moreover, provides mechanical protection for the outlet valve, the tight closure of which is extremely important to ensure a bacteria-free liquid reservoir. The porous insert, which is approximately similar to a sponge, effectively prevents both wilful damage to the valve surfaces and the penetration of contamination, both of which preclude complete closure of the valve.

BRIEF DESCRIPTION OF THE DRAWINGS

Further advantages and aspects of the invention can be gathered from the claims and also from those exemplary embodiments of the invention which are described hereinbelow. In the drawings:

DETAILED DESCRIPTION OF THE EXEMPLARY EMBODIMENTS

Figures 1, 1A:
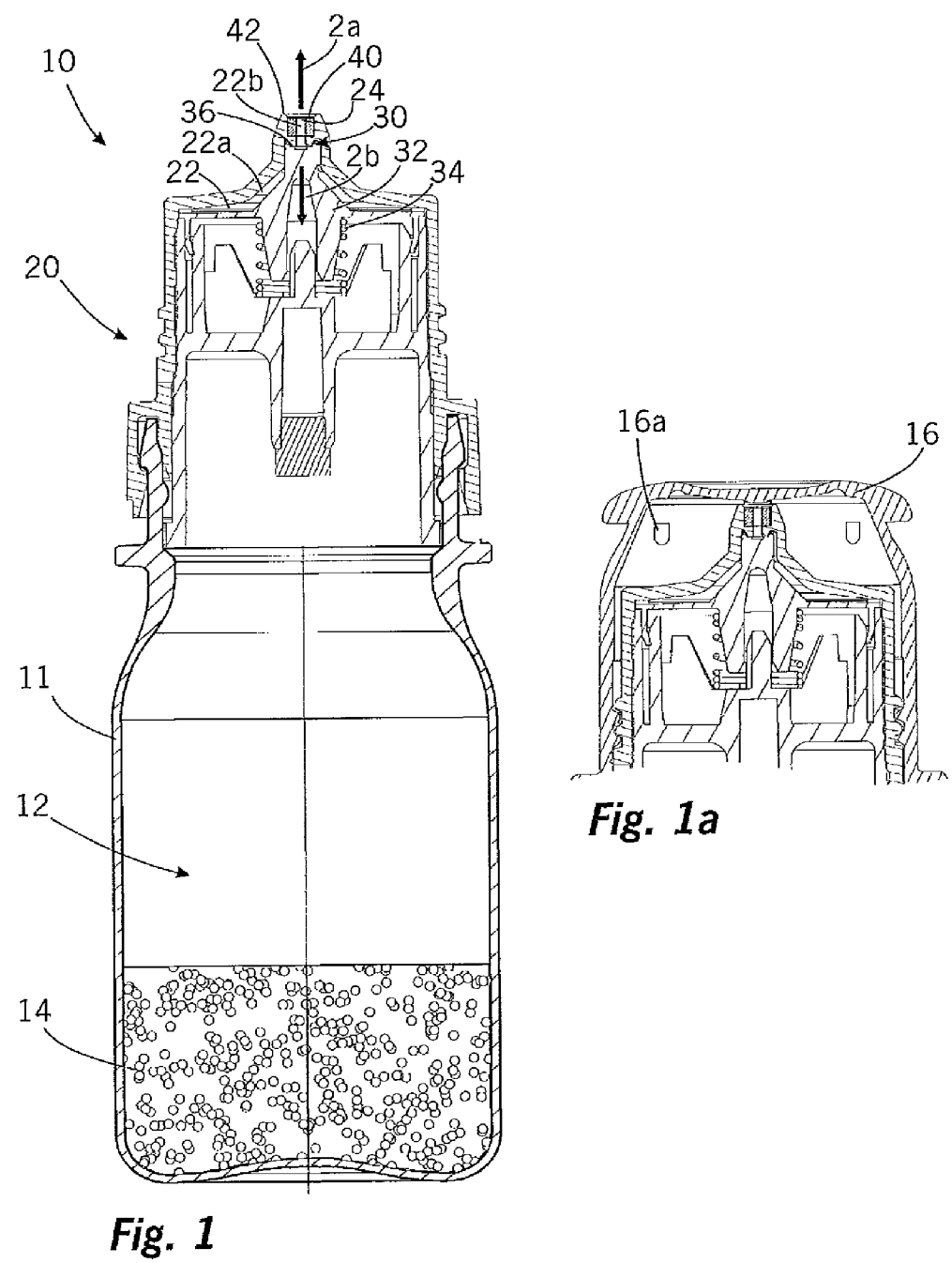
FIG. 1 shows an illustration of a dispenser according to the invention in its entirety.
FIG. 1a shows the outlet subassembly of the dispenser from FIG. 1 with the cap attached.

In the first instance, FIG. 1 shows an illustration of a dispenser according to the invention in its entirety.

This dispenser 10 has a liquid reservoir 12 bounded by a container body 11. An outlet subassembly 20 has been attached to the container body 11 and fastened by means of a latching connection. This outlet subassembly 20 serves to direct liquid, through an outlet channel 22, from the liquid reservoir 12 to a dispensing opening 24. The section plane means that only a final part of said outlet channel 22 is illustrated in FIG. 1.

The dispenser 10 is used by being brought into an upended position with the dispensing opening 24 oriented downward. Walls of the container body 11 are then compressed in order to subject the liquid 14 in the liquid reservoir 12 to pressure. This pressure causes an outlet valve 30, which is provided between the liquid reservoir 12 and the outlet opening 24, to open. The outlet valve 30 comprises a valve body 32, which is pushed permanently in the direction of a valve surface 36 by means of a valve spring 34. As soon as the liquid pressure in a portion 22a of the outlet channel 22 upstream of the outlet valve 30 is sufficiently high, the valve body 32 is displaced in the direction of the arrow 2b by said pressure and releases the path of the liquid into the second portion 22b of the outlet channel 22. The liquid is then directed through the dispensing opening 24 in the direction of the arrow 2a.

The dispenser 10 illustrated is provided in the form of a droplet dispenser for ophthalmic purposes. Therefore, enclosing the dispensing opening 24, there is a droplet-forming surface 40 which is bounded toward the outside by a separation edge 42.

In the unavoidable manner customary of droplet dispensers, once liquid has been dispensed in droplet form, a residual of the liquid, the so-called residual droplet, remains behind on the aforementioned droplet-forming surface 40 and in the second portion 22b of the outlet channel 22. A return flow into the first portion 22a of the outlet channel 22, or into the liquid reservoir 12, is not possible on account of the outlet valve 30 opening in a pressure-dependent manner.

Since it is desired to use the dispenser with a liquid which has only a low level of preservative, or none at all, the liquid residue remaining on the far side of the outlet valve 30 in the second portion 22b of the outlet channel 22, and on the droplet-forming surface 40, is at particular risk of becoming contaminated by germs. This possibility increases if, for the purpose of being dried off quickly, a cap 16 of the dispenser 10 is provided with ventilating openings 16a, which create a permanent connection between the droplet-forming surface 40 and exterior surroundings. Such ventilating openings 16a are illustrated in FIG. 1a.

Figure 2:
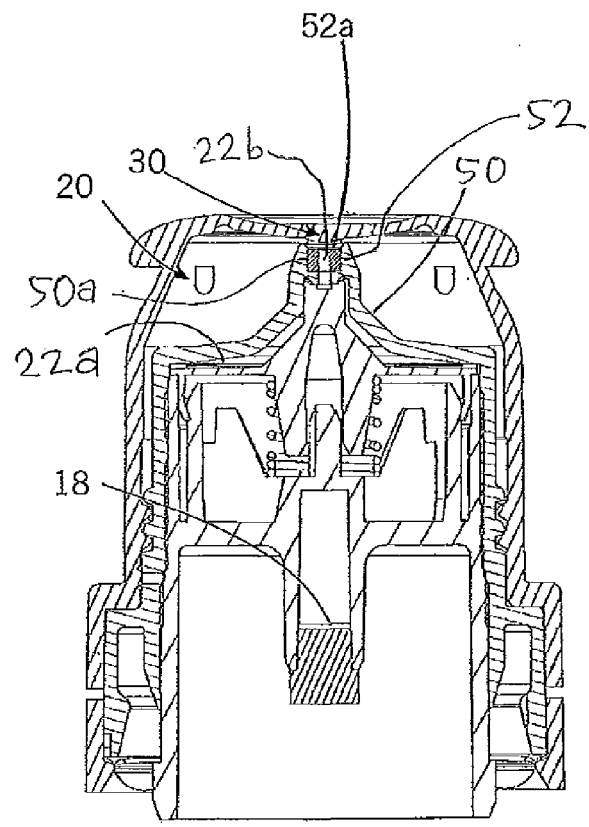
FIGS. 2 to 4 show different outlet subassemblies for the dispenser from FIG. 1.
Figure 3:
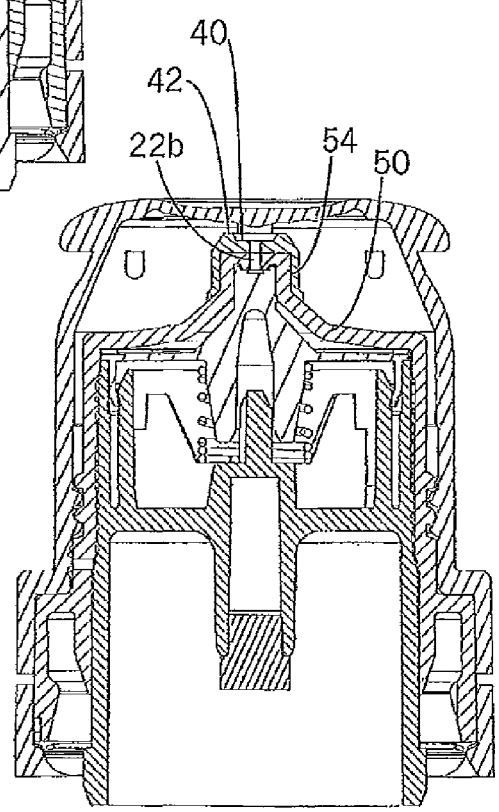
Figure 4:
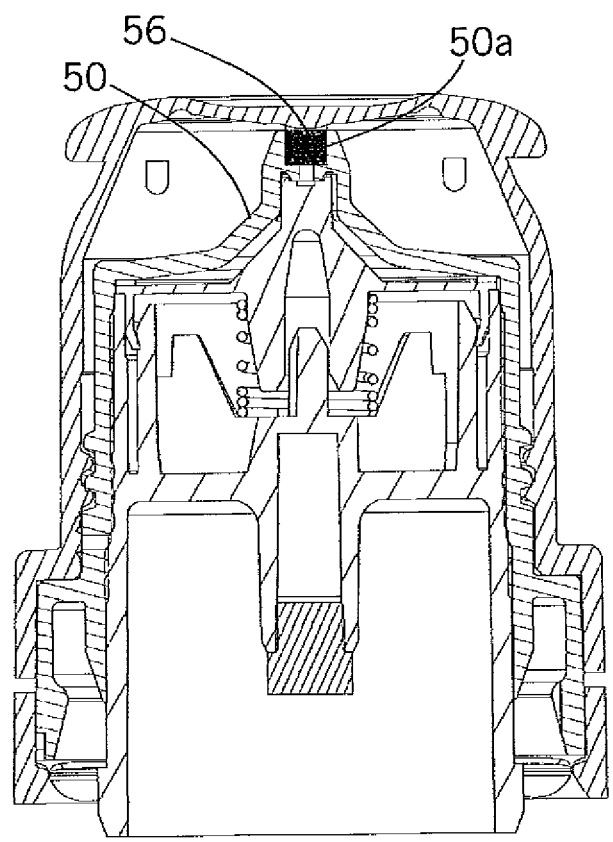

Those configurations of the outlet subassembly 20 which are proposed in FIGS. 2 to 4 are nevertheless beneficial in precluding any risk of unacceptable levels of bacteria being formed in surface regions on the far side of the outlet valve 30.

In the case of the configuration of FIG. 2, which corresponds to that of FIG. 1, a cylindrical aperture 50a is provided in an outer component 50, through which the liquid channel 22 penetrates. An insert 52 in the form of a tube portion has been inserted in said cylindrical aperture 50a. The outer surface of the insert 52 has been adapted to the aperture 50a of the housing component 50 such that a frictionally fitting connection is created by virtue of the insert 52 being pushed into the aperture 50a, the insert 52 remaining securely, as a result of said connection, in its position illustrated in FIG. 2. It would be possible instead, however, to provide a form-fitting connection.

The upper end side 52a of the insert 52 forms an annular surface, which is part of the droplet-forming surface 40. The end side 52 forms the predominant part of the droplet-forming surface 40.

The entire insert 52 is formed from an antibacterial material, that is to say a material which reduces the growth of bacteria, or from a bactericidal material. This is preferably a plastics material which is provided with antibacterially active additives.

Following completion of a dispensing operation, the residual droplet and the liquid residues remaining behind in the second portion 22b remain in close proximity to the antibacterially active surface. The risk of excessive microbial contamination of said liquid residue is therefore low.

At the same time, however, the arrangement of the insert 52 ensures that no liquid which is still arranged upstream of the outlet valve 30 comes into contact with antibacterially active surfaces. The liquid which has not yet flowed past the outlet valve 30 is kept free of germs solely by the inflowing air being filtered by means of a filter 18 and by the sealed configuration of the outlet valve 30. This means that the adverse effect of antibacterial additives which are in permanent contact with the liquid in the liquid reservoir, or in the first portion 22a, is done away with here. There is no risk of additives or any other constituent parts passing into the liquid from antibacterial surfaces and giving rise to adverse effects there.

The configuration of FIG. 3 provides an attachment 54 instead of the insert 52. In the illustrated embodiment the attachment is substantially cup-shaped. It is once again the case that it is only the attachment 54, which has been attached to a housing component 50 through which the outlet channel 22 penetrates, which is produced from an antibacterially active plastics material. Part of the second portion 22b of the outlet channel 22 and also the entire droplet-forming surface 40 together with the separation edge 42 thereof, said edge terminating the droplet-forming surface 40 on the outside, consist of the antibacterially active plastics material. The liquid within the liquid reservoir remains, once again, free of any additives stemming from the plastics material.

In the case of the configuration according to FIG. 4, the component 50, through which the outlet channel penetrates, has the same shaping as in the case of the configuration of FIG. 2. The difference from the configuration of FIG. 2 is that the aperture 50a for accommodating the insert here accommodates a cylindrical porous body 56. This porous body has an approximately sponge-like structure and is, in turn, produced from an antibacterially active material or has been provided subsequently with a coating made of such a material. Here too, the droplet-forming surface 40, part of which is formed by said porous insert 56, and the path of the liquid to the droplet-forming surface 40 are of antibacterial design such that liquid residues remaining on the far side of the outlet valve 30 are not subjected to any inacceptably high levels of contamination. In addition, the fact that the porous material forms active protection against macroscopic contamination means that such contamination cannot reach the outlet valve 30 itself any longer, and thus cannot adversely affect the closing capability of the outlet valve 30. Even wilful damage to the outlet valve, for example by means of a needle, is made much more difficult, if it is possible at all.

The invention claimed is:

1. A dispenser for dispensing pharmaceutical liquid in droplet form, said dispenser comprising:
   an exit opening through which liquid is discharged into a surrounding atmosphere;
   a housing assembly including a housing component and an insert;
   a liquid reservoir disposed within said housing assembly;
   an outlet channel connecting said liquid reservoir to said exit opening; and
   an outlet valve disposed in said outlet channel and openable manually or in a pressure-dependent manner, said outlet valve having a closed position in which said outlet valve separates said outlet channel into a first outlet channel portion disposed upstream of said outlet valve and a second outlet channel portion disposed downstream of said outlet valve, said housing component defining said first outlet channel portion;
   said housing assembly comprising antibacterial material at surfaces disposed to contact liquid downstream of said outlet valve, and it is exclusively said surfaces which comprise said antibacterial material;
   said insert being supported on said housing component, said insert being a separate component from said housing component and being a separate component from said outlet valve, said insert including said surfaces comprising said antibacterial material, a first of said surfaces defining part of said second outlet channel portion and a second of said surfaces defining a first portion of a droplet-forming surface, the droplet-forming surface being disposed in surrounding relation with said exit opening and downstream of said second outlet channel portion, said first portion of said droplet-forming surface being bounded by an edge forming a second portion of said droplet-forming surface;

wherein said housing component defines a recess therein which opens outwardly in a direction away from said outlet valve, said insert being disposed within said recess and being insertable into the recess in a direction opposite to a dispensing direction of the liquid through the exit opening into the surrounding atmosphere.

2. The dispenser according to claim 1, wherein said housing component defines a recess at a terminal end thereof in which said insert is disposed, said recess having a shape conforming to an external shape of said insert, said part of said second outlet channel portion extends through said insert and terminates at said exit opening at said droplet-forming surface.

3. The dispenser according to claim 1, wherein said insert is inserted into and disposed within said housing component.

4. The dispenser according to claim 1, wherein said housing component includes a terminal end in which said recess is disposed, said recess conforming in shape to an external shape of said insert, said terminal end defining thereon said edge forming said second portion of said droplet-forming surface, said part of said second outlet channel portion extends through said insert and terminates at said exit opening at said droplet-forming surface, said exit opening being defined by said insert.

5. The dispenser according to claim 1, wherein said insert comprises a porous material, said part of said second outlet channel portion extends through said porous material to convey liquid from said first outlet channel portion to said exit opening.

6. The dispenser according to claim 1, wherein said first and second surfaces comprise plastic and said antibacterial material comprises an antibacterial additive introduced into said plastic material.

7. The dispenser according to claim 1, wherein said antibacterial material comprises an antibacterially-active coating applied to said first and second surfaces.

8. The dispenser according to claim 1, wherein said insert is annular in configuration and includes an inner wall defining said first surface.

9. The dispenser according to claim 1, wherein said insert includes an end facing in a direction away from said outlet valve, said end defining said second surface and having an annular configuration.

10. The dispenser according to claim 1, wherein said first portion of said droplet-forming surface is recessed inwardly relative to said edge forming said second portion of said droplet-forming surface.

11. The dispenser according to claim 10, wherein said edge is defined on said housing component.

12. A dispenser for dispensing pharmaceutical liquid in droplet form, said dispenser comprising:

an exit opening through which liquid is discharged into a surrounding atmosphere;

a liquid reservoir;

an outlet channel connecting said liquid reservoir to said exit opening;

an outlet valve disposed in said outlet channel and openable manually or in a pressure-dependent manner, said outlet valve having a closed position in which said outlet valve separates said outlet channel into a first outlet channel portion disposed upstream of said outlet valve and a second outlet channel portion disposed downstream of said outlet valve;

a housing assembly including a housing component, part of said second outlet channel portion penetrates through said housing component, said liquid reservoir being disposed within said housing assembly, said housing assembly comprising antibacterial material at surfaces disposed to contact liquid downstream of said outlet valve, and it is exclusively said surfaces which comprise said antibacterial material, said housing assembly further including an attachment separate from said housing component, said attachment being fixed to an outer surface of said housing component at an area thereof disposed immediately adjacent said exit opening, said attachment including said surfaces comprising said antibacterial material.

13. The dispenser according to claim 12, wherein said part of said second outlet channel portion is a first part, and said attachment defines therein a second part of said second outlet channel portion disposed downstream of said first part.

14. The dispenser according to claim 13, wherein said housing component defines therein said first outlet channel portion and includes a terminal end disposed immediately adjacent said exit opening, said attachment being substantially cup-shaped and extending over said terminal end.

15. The dispenser according to claim 12, wherein said part of said second outlet channel portion is a first part, said attachment defines therein a second part of said second outlet channel portion, and said housing component defines therein said first outlet channel portion.

16. The dispenser according to claim 15, wherein a first of said surfaces of said attachment comprising said antibacterial material defines part of a droplet-forming surface disposed in surrounding relation with said exit opening, a second of said surfaces of said attachment comprising said antibacterial material defines a further part of said droplet-forming surface, said first surface being recessed inwardly towards said outlet valve relative to said second surface, said part of said second outlet channel portion is said first part, and a third of said surfaces defines said second part of said second outlet channel portion which penetrates through said attachment and is disposed downstream of said first part.

17. The dispenser according to claim 12, wherein said surfaces of said attachment together define a droplet-forming area, wherein one of said surfaces is an annular surface disposed in surrounding relation with said exit opening and another of said surfaces is an annular edge disposed in surrounding relation with said annular surface, said annular surface being recessed inwardly in a direction towards said outlet valve relative to said annular edge and said exit opening is defined by said attachment.

* * * * *